United States Patent
Tako et al.

(10) Patent No.: US 11,629,354 B2
(45) Date of Patent: Apr. 18, 2023

(54) GRAIN WITH INCREASED NICOTIANAMINE

(71) Applicants: The United States of America, as represented by the Secretary of Agriculture, Washington, DC (US); THE UNIVERSITY OF MELBOURNE, Melbourne (AU)

(72) Inventors: Elad Tako, Brooktondale, NY (US); Jesse T. Beasley, North Melbourne (AU); Alexander Johnson, Abbotsford (AU)

(73) Assignees: The United States of America, as represented by the Secretary of Agriculture, Washington, DC (US); THE UNIVERSITY OF MELBOURNE, Melbourne (AU)

(*) Notice: Subject to any disclaimer, the term of this patent is extended or adjusted under 35 U.S.C. 154(b) by 331 days.

(21) Appl. No.: 16/986,600

(22) Filed: Aug. 6, 2020

(65) Prior Publication Data

US 2021/0238617 A1 Aug. 5, 2021

Related U.S. Application Data

(60) Provisional application No. 62/968,416, filed on Jan. 31, 2020.

(51) Int. Cl.
*A23K 50/70* (2016.01)
*C12N 15/82* (2006.01)
*A23K 10/30* (2016.01)

(52) U.S. Cl.
CPC .......... *C12N 15/8243* (2013.01); *A23K 10/30* (2016.05); *A23K 50/70* (2016.05)

(58) Field of Classification Search
CPC ........ A23K 10/30; A23K 50/70; A23K 50/75; C12N 15/8243
See application file for complete search history.

(56) References Cited

U.S. PATENT DOCUMENTS

2010/0028518 A1* 2/2010 West .................. C11B 5/005
426/544
2013/0305398 A1* 11/2013 Coffin ................ C12N 15/8267
800/320.2

(Continued)

OTHER PUBLICATIONS

Singh, S.P., Keller, B., Gruissem, W., & Bhullar, N.K. (2016). Rice Nicotianamine Synthase 2 expression improves dietary iron and zinc levels in wheat. TAG. Theoretical and Applied Genetics. Theoretische Und Angewandte Genetik, 130, 283-292. (Year: 2016).*

(Continued)

*Primary Examiner* — Walter A Moore
(74) *Attorney, Agent, or Firm* — John Fado; Ariel Atkinson

(57) ABSTRACT

A grain crop may have an increased amount of nicotianamine (NA). The increased NA may correlate with an increased bioavailability of iron in the grain and any product, such as ground flour, resulting from processing of the grain. The increase of NA may be achieved through the expression of the OsNAS2 gene. Further, a grain flour produced from a transformed grain plant may have an increased amount of NA, and thus an increased amount of bio-available iron, as compared to a grain flour produced from a non-transformed grain plant of the same species. The grain flour produced from the transformed grain plant ("biofortified flour") may be used in food production for feed to animals or humans. Such a feed including the biofortified flour may improve the gut health and/or the feed efficiency of the eater as compared to the gut health for an eater of non-biofortified flour.

5 Claims, 12 Drawing Sheets
(6 of 12 Drawing Sheet(s) Filed in Color)
Specification includes a Sequence Listing.

(56) References Cited

U.S. PATENT DOCUMENTS

| | | | |
|---|---|---|---|
| 2014/0378755 A1* | 12/2014 | Bangera | A01K 67/027 |
| | | | 435/6.11 |
| 2015/0080296 A1* | 3/2015 | Silver | A61P 3/02 |
| | | | 514/5.5 |
| 2018/0125808 A1* | 5/2018 | Ala'Aldeen | A23K 50/10 |

OTHER PUBLICATIONS

Beasley et al., Nicotianamine-chelated iron positively affects iron status, intestinal morphology and microbial populations in vivo (Gallus gallus); Sci Rep 10, 2297 (2020). (Year: 2020).*

* cited by examiner

| Variable | Diet | Baseline | Week 1 | Week 2 | Week 3 | Week 4 | Week 5 | Week 6 |
|---|---|---|---|---|---|---|---|---|
| Body Weight (kg) | Control | 0.125 ± 0.007 | 0.158 ± 0.004 | 0.195 ± 0.007 | 0.236 ± 0.010 | 0.286 ± 0.013 | 0.355 ± 0.016 | 0.365 ± 0.029 |
| | Biofortified | 0.122 ± 0.006 | 0.160 ± 0.004 | 0.191 ± 0.007 | 0.222 ± 0.010 | 0.260 ± 0.014 | 0.318 ± 0.018 | 0.353 ± 0.029 |
| Hb (g/L) | Control | 72.7 ± 2.3 | 96.5 ± 1.6 | 112.2 ± 1.2*** | 103.5 ± 3.5 | 99.6 ± 3.7 | 82.4 ± 3.7 | 94.9 ± 3.6 |
| | Biofortified | 72.7 ± 2.3 | 93.2 ± 1.6 | 92.5 ± 1.5 | 97.8 ± 3.7 | 104.7 ± 4.0 | 91.4 ± 3.4 | 101.2 ± 3.5 |
| Total Body Hb (mg) | Control | 2.59 ± 0.14 | 4.26 ± 0.124 | 6.15 ± 0.17*** | 7.09 ± 0.35 | 7.87 ± 0.33 | 8.48 ± 0.67 | 9.83 ± 1.01 |
| | Biofortified | 2.52 ± 0.13 | 4.20 ± 0.124 | 4.72 ± 0.17 | 6.21 ± 0.39 | 7.57 ± 0.36 | 7.74 ± 0.70 | 10.06 ± 0.98 |
| HME (%) | Control | | 12.16 ± 0.879 | 13.80 ± 0.67*** | 10.21 ± 0.77 | 8.32 ± 0.50 | 4.36 ± 0.76 | 3.14 ± 1.02 |
| | Biofortified | | 11.17 ± 0.879 | 7.14 ± 0.71 | 8.56 ± 0.85 | 8.41 ± 0.55 | 4.65 ± 0.76 | 5.84 ± 1.00 |
| FCR | Control | | 5.85 ± 0.738 | 4.82 ± 0.55 | 6.10 ± 0.52 | 7.98 ± 0.51 | 4.09 ± 0.24 | 22.30 ± 3.19 |
| | Biofortified | | 4.86 ± 0.736 | 5.98 ± 0.55 | 6.14 ± 0.57 | 6.89 ± 0.53 | 3.63 ± 0.25 | 19.81 ± 2.99 |
| Feed Intake (g) | Control | | 180.6 ± 20.0 | 157.8 ± 13.3 | 251.0 ± 27.4 | 299.9 ± 41.9 | 284.5 ± 29.8 | 243.7 ± 25.2 |
| | Biofortified | | 171.0 ± 20.0 | 152.6 ± 13.3 | 201.3 ± 27.4 | 244.8 ± 41.9 | 190.8 ± 29.8 | 185.6 ± 21.8 |
| Cumulative Feed Intake (g) | Control | | | 338.5 ± 31.6 | 589.5 ± 50.7 | 889.4 ± 91.2 | 1174.0 ± 119.0 | 1333.0 ± 153.0 |
| | Biofortified | | | 323.6 ± 31.6 | 524.9 ± 50.7 | 769.7 ± 91.2 | 960.0 ± 119.0 | 1096.0 ± 153.0 |
| Cumulative FCR | Control | | | 4.56 ± 0.38 | 5.00 ± 0.39 | 5.45 ± 0.63 | 4.92 ± 0.52 | 6.12 ± 0.85 |
| | Biofortified | | | 5.15 ± 0.38 | 5.25 ± 0.39 | 4.73 ± 0.63 | 4.16 ± 0.52 | 4.66 ± 0.73 |

FIG. 9

LDA Score (log 10)

SEQUENCE LISTING

```
<160> NUMBER OF SEQ ID NOS: 16

<210> SEQ ID NO 1
<211> LENGTH: 42
<212> TYPE: DNA
<213> ORGANISM: artificial sequence
<220> FEATURE:
<223> OTHER INFORMATION: Chemically Synthesized

<400> SEQUENCE: 1
ttcaacatca ttccaagcag cacgtaaccc aaaatgccct tg                          42

<210> SEQ ID NO 2
<211> LENGTH: 39
<212> TYPE: DNA
<213> ORGANISM: artificial sequence
<220> FEATURE:
<223> OTHER INFORMATION: Chemically Synthesized

<400> SEQUENCE: 2
cagattggca acggctacgc ggacagcaaa acgaccaag                              39

<210> SEQ ID NO 3
<211> LENGTH: 40
<212> TYPE: DNA
<213> ORGANISM: artificial sequence
<220> FEATURE:
<223> OTHER INFORMATION: Chemically Synthesized

<400> SEQUENCE: 3
ggacagctta ggcgaggaat gctggggctt ccttaatctc                             40
```

<210> SEQ ID NO 4
<211> LENGTH: 39
<212> TYPE: DNA
<213> ORGANISM: artificial sequence
<220> FEATURE:
<223> OTHER INFORMATION: Chemically Synthesized

<400> SEQUENCE: 4
aagggtggat ggtgatagcc ttgatgttgc catgtgccc                     39

<210> SEQ ID NO 5
<211> LENGTH: 38
<212> TYPE: DNA
<213> ORGANISM: artificial sequence
<220> FEATURE:
<223> OTHER INFORMATION: Chemically Synthesized

<400> SEQUENCE: 5
gttccagaag gcggaagagt aacgatcggg gaaattcg                      38

<210> SEQ ID NO 6
<211> LENGTH: 40
<212> TYPE: DNA
<213> ORGANISM: artificial sequence
<220> FEATURE:
<223> OTHER INFORMATION: Chemically Synthesized

<400> SEQUENCE: 6
gaatgacgtc cgaggagaag cgatatcgtc cagctccact                    40

<210> SEQ ID NO 7
<211> LENGTH: 39
<212> TYPE: DNA
<213> ORGANISM: artificial sequence
<220> FEATURE:
<223> OTHER INFORMATION: Chemically Synthesized

<400> SEQUENCE: 7
cggcttcctg tacccatcc tccatcttgg tggagaagc                      39

<210> SEQ ID NO 8
<211> LENGTH: 40
<212> TYPE: DNA
<213> ORGANISM: artificial sequence
<220> FEATURE:
<223> OTHER INFORMATION: Chemically Synthesized

<400> SEQUENCE: 8
tccagaagat caccggactc cgagcatgtc ggagtagtgc                    40

<210> SEQ ID NO 9
<211> LENGTH: 37
<212> TYPE: DNA
<213> ORGANISM: artificial sequence
<220> FEATURE:
<223> OTHER INFORMATION: Chemically Synthesized

<400> SEQUENCE: 9
gtcttcctgg ccgcacttgt tcaccacgtc gtcgtct                       37

<210> SEQ ID NO 10
<211> LENGTH: 39
<212> TYPE: DNA
<213> ORGANISM: artificial sequence
<220> FEATURE:

<223> OTHER INFORMATION: Chemically Synthesized

<400> SEQUENCE: 10
gcgggttcct atacccgatt gcatgtcctt cgacttgtg                          39

<210> SEQ ID NO 11
<211> LENGTH: 45
<212> TYPE: DNA
<213> ORGANISM: artificial sequence
<220> FEATURE:
<223> OTHER INFORMATION: Chemically Synthesized

<400> SEQUENCE: 11
ctcttcaccg acctggtcac tgtagttgct gtagtagggg aagat                   45

<210> SEQ ID NO 12
<211> LENGTH: 38
<212> TYPE: DNA
<213> ORGANISM: artificial sequence
<220> FEATURE:
<223> OTHER INFORMATION: Chemically Synthesized

<400> SEQUENCE: 12
gaggcgggtt cgaggtgctc caccatctcg ccgaacct                           38

<210> SEQ ID NO 13
<211> LENGTH: 37
<212> TYPE: DNA
<213> ORGANISM: artificial sequence
<220> FEATURE:
<223> OTHER INFORMATION: Chemically Synthesized

<400> SEQUENCE: 13
gaggaggccc tggtgaagag gatgcaggac gtcacca                            37

<210> SEQ ID NO 14
<211> LENGTH: 40
<212> TYPE: DNA
<213> ORGANISM: artificial sequence
<220> FEATURE:
<223> OTHER INFORMATION: Chemically Synthesized

<400> SEQUENCE: 14
cacattgccc ctgtcttgtc ctgggtccgt tgagacgtta                         40

<210> SEQ ID NO 15
<211> LENGTH: 39
<212> TYPE: DNA
<213> ORGANISM: artificial sequence
<220> FEATURE:
<223> OTHER INFORMATION: Chemically Synthesized

<400> SEQUENCE: 15
ggacccagca accttcattg atccttctgg cttgtgagg                          39

<210> SEQ ID NO 16
<211> LENGTH: 37
<212> TYPE: DNA
<213> ORGANISM: artificial sequence
<220> FEATURE:
<223> OTHER INFORMATION: Chemically Synthesized

<400> SEQUENCE: 16
atggaggagt gccacaggag taggcgcaca gctggat                            37

GRAIN WITH INCREASED NICOTIANAMINE

CROSS-REFERENCE TO RELATED APPLICATIONS

This application claims the benefit of U.S. Provisional Application No. 62/968,416, filed Jan. 31, 2020, which is incorporated herein by reference in its entirety.

BACKGROUND

Iron (Fe) supplementation and fortification are widely used strategies to combat Fe deficiencies worldwide. Iron supplementation involves large dose delivery of highly absorbable (bioavailable) Fe and is effective in treating severe cases of Fe deficiency anemia. Iron fortification involves low dose delivery of bioavailable Fe fortificants to food products during manufacture (or point-of-use) and is an effective strategy to boost Fe intakes. Iron fortification of wheat flour is now mandatory in 75 countries worldwide. However, the tendency of Fe fortificants such as ferrous sulfate ($FeSO_4$) to oxidize and cause undesired organoleptic and sensory properties pose significant challenges. Almost 90% of countries utilize fortificants with poor bioavailability or fortify at sub-optimal concentrations. Iron chelated by ethylenediaminetetraacetate (EDTA) is a commonly recommended fortificant for cereal flour to minimize sensory alterations while providing Fe in a bioavailable form. Unfortunately, the cost of using appropriately chelated Fe fortificants ($2 USD per ton to fortify wheat flour with EDTA-chelated Fe), and the requirement for centralized cereal processing and industrial milling limits flour fortification programs in less developed countries. Furthermore, and perhaps more importantly, both supplementation and fortification frequently deliver excess dietary Fe to the intestinal lumen which can cause severe gastrointestinal disruption, dysbiosis and the proliferation of non-beneficial gut bacteria.

Nicotianamine (NA) is a non-protein amino acid that functions as an endogenous chelator of Fe, zinc (Zn) and other transition metals in higher plants. In graminaceous cereals NA serves as the biosynthetic precursor to 2'-deoxymugenic acid (DMA), a related Fe chelator in plant tissues that also functions as a root-secreted phytosiderophore to chelate ferric Fe in the rhizosphere. Both NA and/or DMA are major Fe chelators in white wheat (*Triticum aestivum* L.) flour and enhancers of in vitro Fe bioavailability and increased NA/DMA biosynthesis has been employed to biofortify wheat and rice (*Oryza sativa* L.) with Fe and Zn. While both NA and DMA chelate ferric ($Fe^{3+}$) ions, only NA is capable of chelating highly-bioavailable $Fe^{2+}$ ions. Iron biofortified rice with increased NA biosynthesis has also reversed anemia symptoms in mice, suggesting that NA-chelated Fe is bioavailable in vivo.

However, no in vivo studies have confirmed the effects of NA-fortified wheat on an animal or human system.

All of the references cited herein, including U.S. Patents and U.S. Patent Application Publications, are incorporated by reference in their entirety.

Mention of trade names or commercial products in this publication is solely for the purpose of providing specific information and does not imply recommendation or endorsement by the U.S. Department of Agriculture.

SUMMARY

A grain crop may have an increased amount of nicotianamine (NA). The increased NA may correlate with an increased bioavailability of iron in the grain and any product, such as ground flour, resulting from processing of the grain.

Further, a grain flour produced from a transformed grain plant may have an increased amount of NA, and thus an increased amount of bio-available iron, as compared to a grain flour produced from a non-transformed grain plant of the same species. The grain flour produced from the transformed grain plant ("biofortified flour") may be used in food production for feed to animals or humans. Such a feed including the biofortified flour may improve the gut health of the eater as compared to the gut health for an eater of non-biofortified flour.

The increase of NA may be achieved through the expression of the OsNAS2 gene.

SEQUENCE LISTING

The Sequence Listing submitted via EFS-Web as an ASCII compliant text file format (.txt) filed Sep. 30, 2020, named "0104.19 Sequence Listing_ST25.txt" (created on Sep. 30, 2020, 4 kb), is hereby incorporated herein by reference in its entirety. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BRIEF DESCRIPTION OF THE FIGURES

Advantages of embodiments of the present invention will be apparent from the following detailed description of the exemplary embodiments. The patent or application file contains at least one drawing executed in color. Copies of this patent or patent application publication with color drawing(s) will be provided by the office upon request and payment of the necessary fee.

The following detailed description should be considered in conjunction with the accompanying figures in which:

Exemplary

Exemplary

Exemplary

Exemplary

Exemplary

Exemplary

Exemplary

Exemplary

Exemplary FIG. 9 shows body weight, biomarkers of Fe status and feed consumption throughout the study. Values represent mean±SEM of at least nine biological replicates. Asterisks denote significant differences between diet treatments for p<0.001 (***) as determined by Student's t-test. Photos show examples of Control (left) and Biofortified (right) chickens at each week. Hb: hemoglobin, HME: hemoglobin maintenance efficiency, FCR: feed conversion ratio.

Exemplary

Exemplary FIG. 11A shows chicken intestinal goblet cell number and diameter (μm). FIG. 11B shows chicken intestinal villi length and width (μm). FIG. 11C shows cecal short-chain fatty acid (SCFA) composition. Bars represent mean±SEM of nine biological replicates. FIGS. 11D and 11E show relative abundance of microbial populations at the levels of phyla (11D); and families and genera (11E). Asterisks denote significant differences for p<0.05 (*), p≤0.001 (***) as determined by Student's t-test. AU: arbitrary units.

Exemplary FIG. 12A shows microbial α-diversity of chicken ceca using Faith's phylogenetic diversity (PD). FIG. 12B shows microbial β-diversity of chicken ceca using unweighted UniFrac distances separated by three principal components (PC). Each dot represents either a Control (green) or Biofortified (red) chicken. FIG. 12C shows computed linear discriminant analysis (LDA) scores of differences in microbial relative abundance and metabolic capacity, respectively. Positive LDA scores (green) are enriched in Control and negative LDA scores (red) are enriched in Biofortified. Asterisks denote significant differences for p<0.05 (*) as determined by Kruskal-Wallis test.

DETAILED DESCRIPTION

Figure 1:
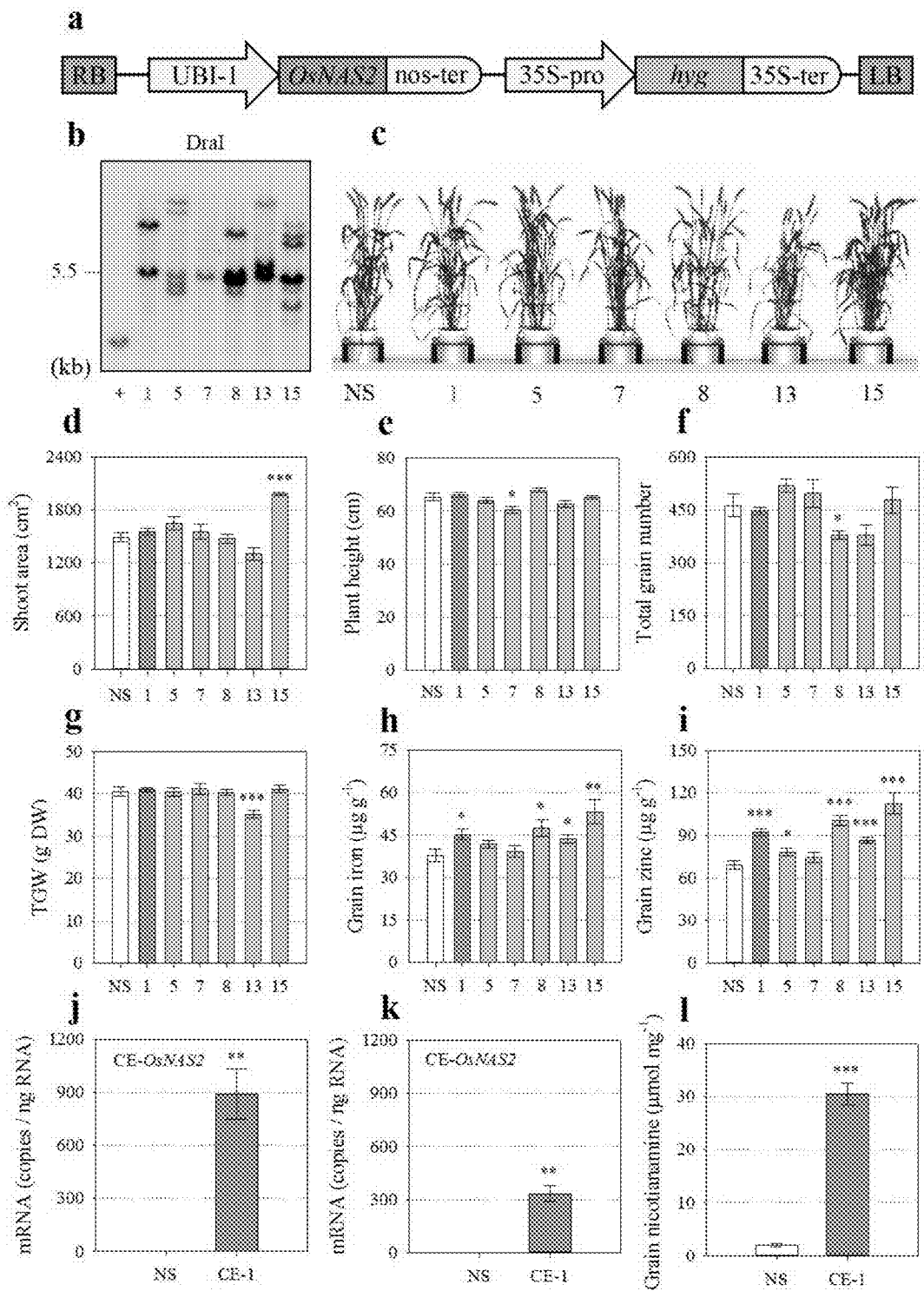
FIG. 1 shows the generation and characterization of independent bread wheat transformation events constitutively expressing the rice nicotianamine synthase 2 (OsNAS2) gene. (a) Schematic representation of the T-DNA construct. RB and LB: right and left borders, respectively; UBI-1: maize ubiquitin 1 promoter; OsNAS2: rice nicotianamine synthase 2 gene (LOC_Os03g19420); nos-ter: nopaline synthase terminator; 35S-pro: dual promoter of 35S cauliflower mosaic virus gene; hyg: hygromycin phosphotransferase gene; 35S-ter: terminator of 35S cauliflower mosaic virus gene. (b) Southern blot analysis of $T_0$ wheat events to determine T-DNA insertion number. DraI: restriction endonuclease; + indicates positive control. (c) Representative plants of null segregant (NS) and the 6 transformation events (CE-OsNAS2) 100 days after sowing. (d-g) Projected shoot area ($cm^2$), plant height (cm), total grain number and thousand grain weight (TGW) of NS (white), leading CE-OsNAS2 event (CE-1, orange) and other CE-OsNAS2 events (grey) at the $T_1$ generation. Bars represent mean±SEM of at least 7 biological replicates. (h-i) Iron and zinc concentration ($\mu g\ g^{-1}$ DW) in $T_2$ whole grain of NS, CE-1 and other CE-OsNAS2 events. Bars represent mean±SEM of at least 7 biological replicates. (j-k) Relative quantification of OsNAS2 transcript levels in NS and CE-1 shoots and roots. Bars represent mean±SEM of three bulked biological replicates, each with three technical replicates of quantitative RT-PCR. (1) Nicotianamine concentration ($\mu mol\ mg^{-1}$) in whole grain of NS and CE-1 plants at the $T_2$ generation. Bars represent mean±SEM of three biological replicates. Asterisks denote the significance between NS and CE-OsNAS2 events for P<0.05 (*), P≤0.01 (), P≤0.001 (*) as determined by student's t-test. Wild-type plants did not differ from NS plants for any trait measured and therefore only NS data is presented.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

The amounts, percentages, and ranges disclosed herein are not meant to be limiting, and increments between the recited amounts, percentages, and ranges are specifically envisioned as part of the invention.

"Optional" or "optionally" means that the subsequently described event or circumstance may or may not occur, and that the description includes instances in which said event or circumstance occurs and instances where it does not. For example, the phrase "optionally comprising X" means that the composition may or may not contain X, and that this description includes compositions that contain and do not contain X.

The term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

According to at least one exemplary embodiment, a grain crop may have an increased amount of nicotianamine (NA). The increased NA may correlate with an increased bioavailability of iron in the grain and any product, such as ground flour, resulting from processing of the grain.

According to another exemplary embodiment of the invention, a grain flour produced from a transformed grain plant may have an increased amount of NA as compared to a grain flour produced from a non-transformed grain plant of the same species. The grain flour produced from the transformed grain plant may be used in food production for feed to animals or humans.

The increase of NA may be achieved through the expression of the OsNAS2 gene.

Example 1: Creation of Transformed Wheat

The full-length coding sequence of OsNAS2 (LOC_Os03g19420) was PCR amplified from rice (*Oryza sativa* L.) cv. Nipponbare genomic DNA. Recombination into a modified pMDC32 vector with the hygromycin phosphotransferase plant-selectable marker gene placed OsNAS2 under transcriptional control of the maize (*Zea mays* L.) ubiquitin 1 promoter (FIG. 1a). Particle bombardment of the construct into immature wheat (*Triticum aestivum* L.) cv. Bobwhite embryos (1.0-1.5 mm in length) was performed using established protocols (Kovalchuk, N. et al. Characterization of the wheat endosperm transfer cell-specific protein TaPR60. *Plant Mol. Biol.* 71, 81-98 (2009)). Plants were grown in glasshouse conditions (12 hr photoperiod, 23° C. day/12° C. night, 50% humidity) in soil (coconut peat and sand mixture) with complete fertilizers. This process created wheat with constitutive expression of the OsNAS2 gene ("CE-OsNAS2 wheat"). Six independent CE-OsNAS2 events termed CE-1, CE-5, CE-7, CE-8, CE-13 and CE-15 were regenerated from tissue culture.

For an insert copy number analysis, genomic DNA (10 μg) was isolated from CE-OsNAS2 leaf tissue and digested with DraI and HindIII restriction enzymes. Restriction fragments were separated by gel electrophoresis (0.8% agarose) alongside a positive barley control and blotted to a nylon membrane. Two independent hybridizations of a $^{32}$P-labelled probe to both the nopaline synthase terminator and dual 35S promoter were performed using established protocols (Pallotta, M. et al. Molecular basis of adaptation to high soil boron in wheat landraces and elite cultivars. *Nature* 514, 88-91 (2014)). The resulting copy number ranged from 1-7 among the six events (FIG. 1b).

For phenotyping of $T_1$ progeny, grain were sown in white plastic pots (14×19 cm) containing 2.5 kg of soil mixture (equal parts clay-loam soil and coconut peat) and Osmocote® fertilizer. Plants were maintained under glasshouse conditions (12 hr photoperiod, 24° C. day/18° C. night, 50-90% humidity). Projected shoot area and plant height was measured 100 days after sowing using a conveyer automated imaging system. Grain number and thousand grain weight (TGW) were manually determined at harvest.

Two of the events (CE-1 and CE-5) showed no phenotypic differences from a null segregant (NS) line derived from CE-1 nor from wild-type (WT) wheat with regard to shoot area, plant height, total grain number and thousand grain weight (FIG. 1c-g). WT plants did not differ from NS plants in any trait measured, including iron and zinc content discussed below.

Quantitative reverse transcription PCR (qRT-PCR) was also performed to measure expression levels. Shoot and root tissues (without the crown) of 4-week-old plants were separated, cleaned with deionized $H_2O$ and snap frozen. Three plants of each genotype (representing one biological replicate) were combined and total RNA was extracted from pulverized frozen plant tissue (100-150 mg) using TRIzol Reagent (Life Technologies, Carlsbad, Calif., USA) and a commercial kit (Direct-zol™, ZymoResearch). Genomic DNA was removed from RNA (2 μg) using a DNAse I treatment (Promega) and reverse transcription was performed using a commercial kit (Bioline).

Consensus primers were designed to amplify homeologous groups of TaNAS, TaNAAT and TaDMAS gene families using Primer3 software. Each biological replicate was analyzed in triplicate and transcripts were quantified against four replicates of ten-fold serial dilutions ($10^2$-$10^8$) for each purified PCR template (DNA Clean & Concentrator™-5, ZymoResearch). Expression levels of OsNAS2, TaNAS, TaNAAT and TaDMAS were measured in root and shoot tissues using qRT-PCR analysis (CFX384—BioRad). The geometric mean expression of three housekeeping genes: TaCyclophilin, TaGAPDH and TaELF, and TaGAPDH, TaActin, and TaELF, was used to normalize OsNAS2, TaNAS, TaNAAT, and TaDMAS gene expression within shoot and root tissues, respectively. All primers had annealing temperatures between 61-65° C. and primer sequences and efficiencies are provided in the listing in Table 1 below:

TABLE 1

Primer information for quantitative reverse transcription PCR (qRT-PCR) analysis in CE::OsNAS2 and NS seedling shoot and root tissues. The table provides gene name, forward and reverse primer sequences, qRT-PCR primer efficiency (%) and PCR product length (bp).

| Gene Name | Forward primer sequence (5'-3') | Reverse primer sequence (5'-3') | Primer Efficiency (%) | Product length (bp) |
|---|---|---|---|---|
| TaGAPDH | TTCAACATCATTCCAAGCAGCA | CGTAACCCAAAATGCCCTTG | 98.1 | 220 |
| TaELF | CAGATTGGCAACGGCTACG | CGGACAGCAAAACGACCAAG | 96.3 | 227 |
| TaWIN | GGACAGCTTAGGCGAGGAAT | GCTGGGGCTTCCTTAATCTC | 97.7 | 126 |
| TaVIP2 | AAGGGTGGATGGTGATAGCC | TTGATGTTGCCATGTGCCC | 98.6 | 138 |
| UbiOsNAS2 | GTTCCAGAAGGCGGAAGAGT | AACGATCGGGGAAATTCG | 95 | 166 |
| TaNAS1 | GAATGACGTCCGAGGAGAAG | CGATATCGTCCAGCTCCACT | 98.3 | 135 |
| TaNAS2 | CGGCTTCCTGTACCCCATC | CTCCATCTTGGTGGAGAAGC | 97.7 | 216 |
| TaNAS3 | TCCAGAAGATCACCGGACTC | CGAGCATGTCGGAGTAGTGC | 96 | 225 |
| TaNAS4 | GTCTTCCTGGCCGCACTT | GTTCACCACGTCGTCGTCT | 99.6 | 213 |
| TaNAS5 | GCGGGTTCCTATACCCGAT | TGCATGTCCTTCGACTTGTG | 99.7 | 130 |
| TaNAS6 | CTCTTCACCGACCTGGTCAC | TGTAGTTGCTGTAGTAGGGGAAGAT | 99.2 | 208 |
| TaNAS7 | GAGGCGGGTTCGAGGTGCTC | CACCATCTCGCCGAACCT | 92.6 | 179 |
| TaNAS9 | GAGGAGGCCCTGGTGAAGA | GGATGCAGGACGTCACCA | 99.1 | 118 |
| TaNAAT1 | CACATTGCCCCTGTCTTGTC | CTGGGTCCGTTGAGACGTTA | 97.3 | 160 |
| TaNAAT2 | GGACCCAGCAACCTTCATT | GATCCTTCTGGCTTGTGAGG | 96.7 | 165 |

TABLE 1-continued

Primer information for quantitative reverse transcription PCR (qRT-PCR) analysis in CE::OsNAS2 and NS seedling shoot and root tissues. The table provides gene name, forward and reverse primer sequences, qRT-PCR primer efficiency (%) and PCR product length (bp).

| Gene Name | Forward primer sequence (5'-3') | Reverse primer sequence (5'-3') | Primer Efficiency (%) | Product length (bp) |
|---|---|---|---|---|
| TaDMAS | ATGGAGGAGTGCCACAGG | AGTAGGCGCACAGCTGGAT | 96.1 | 193 |

Example 2: Characterization of Transformed Wheat

To characterize the transformed wheat produced and described in the above method, the amount of iron and zinc accumulated in the grain was studied. Further, field trials were performed to compare the null segregant (NS) line with three CE-1 sibling lines (designated CE-1.1, CE-1.2, and CE-1.3). These field trials were conducted in Katanning and Merredin, Western Australia.

For analysis of iron and zinc, plants were grown in glasshouse conditions (12 hr photoperiod, 18° C. day/13° C. night, 40-80% humidity) in Hortico® potting mix with Osmocote® fertilizer. The main stem flag leaf, rachis, bracts and grain were harvested at 5-8 DAA (days after anthesis), 12-15 DAA, 19-21 DAA, 26-29 DAA and maturity. Samples were washed, oven dried for 48 hr at 60° C. and ground to a powder before analysis by inductively coupled plasma mass spectrometry (ICP-MS).

Elemental analysis showed that four of the CE-OsNAS2 events (CE-1, CE-8, CE-13, CE-15) produced $T_2$ grain with significantly increased Fe and Zn concentrations relative to NS and WT and one CE-OsNAS2 event (CE-5) produced $T_2$ grain with significantly increased Zn concentration relative to NS and WT (FIG. 1*h-i*).

Based on low insert copy number, no difference in plant phenotype, and increased grain Fe and Zn concentrations from the $T_0$ to $T_2$ generations, homozygous progeny of the double-insert event CE-1 and corresponding NS line were selected for a range of additional analyses from the $T_3$ to $T_6$ generation. Glasshouse-grown CE-1 seedlings displayed high OsNAS2 expression in roots and shoots (FIG. 1*j-k*). Expression of a range of endogenous TaNAS, TaNAAT and TaDMAS genes involved in NA and DMA biosynthesis was not significantly different between CE-1 and NS seedlings, however, a trend towards slightly reduced expression was detected in CE-1. The CE-1 and NS seedlings did not differ with respect to shoot Fe, Zn and DMA concentration while shoot NA concentration was 1.3-fold higher in CE-1 seedlings. Nicotianamine concentration was 15-fold higher in CE-1 mature grain relative to NS (FIG. 1*l*).

Figure 2:
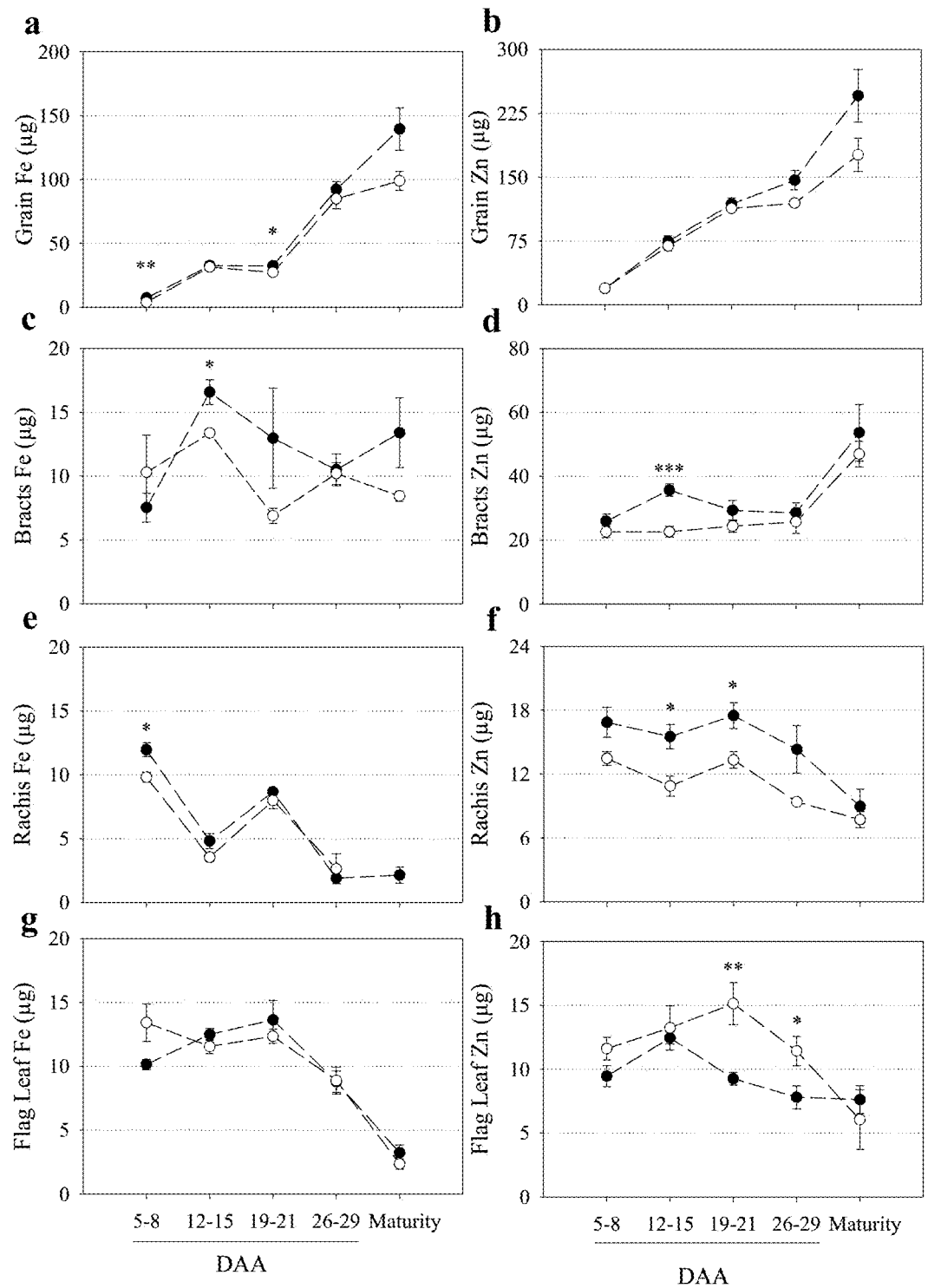
FIG. 2 shows iron and zinc content in vegetative and grain tissues during grain filling of CE-OsNAS2 and NS wheat lines. Fe and Zn content (μg) in NS (open circles) and CE-1 (closed circles) plant tissues between 5-8, 12-15, 19-21 and 26-29 days after anthesis (DAA) as well as at maturity. (a-b) grain; (c-d) bracts; (e-f) rachis; and (g-h) flag leaf tissues were sampled for Fe and Zn content, respectively. Each symbol represents mean±SEM of at least 3 biological replicates. Asterisks denote the significance between NS and CE-1 for P<0.05 (*), P≤0.01 (), P≤0.001 (*) as determined by student's t-test.

The CE-1 grain had significantly higher Fe content at 5-8 days after anthesis (DAA) and 19-21 DAA relative to NS grain (P=0.006 and P=0.046; respectively) and showed non-significant trends towards higher grain Fe and Zn content at maturity (FIG. 2*a-b*).

Elemental X-ray fluorescence (XRF) maps of Fe, Zn, Cu and Mn in transverse cross-sections of two representative CE-1 and NS grain (4 sets of maps total) were collected. Briefly, the beam energy was set at 15.6 keV and the beam focused to approximately 2×μm² using Kirkpatrick-Baez mirrors. Samples were analyzed continuously in the horizontal direction with a sampling interval of 4 μm and a step size of 4 μm in the vertical direction (pixel transit time was set at 5.2 ms). The XRF signal from the 80 μm transverse grain sections was collected using a 384-element Maia detector system. Tri-color elemental maps showing the distribution of Fe, Zn and P near the grain edge of one representative CE-1 and NS grain (2 sets of maps total; different grain from those used with the Maia detector) were collected using a separate Vortex-EM detector. The tri-color maps were used as guides to select rectangular areas of approximately 14×140 μm near the grain edge for the generation of Fe, Zn, P and S line scans. Elemental maps were generated using GeoPIXE software. The NS grain contained 38 μg g$^{-1}$ DW Fe, 71 μg g$^{-1}$ DW Zn, 4700 μg g$^{-1}$ DW P and 1630 μg g$^{-1}$ DW S while CE-1 grain contained 69 μg g$^{-1}$ DW Fe, 122 μg g$^{-1}$ DW Zn, 5300 μg g$^{-1}$ DW P and 2100 μg g$^{-1}$ DW S.

Figure 3:
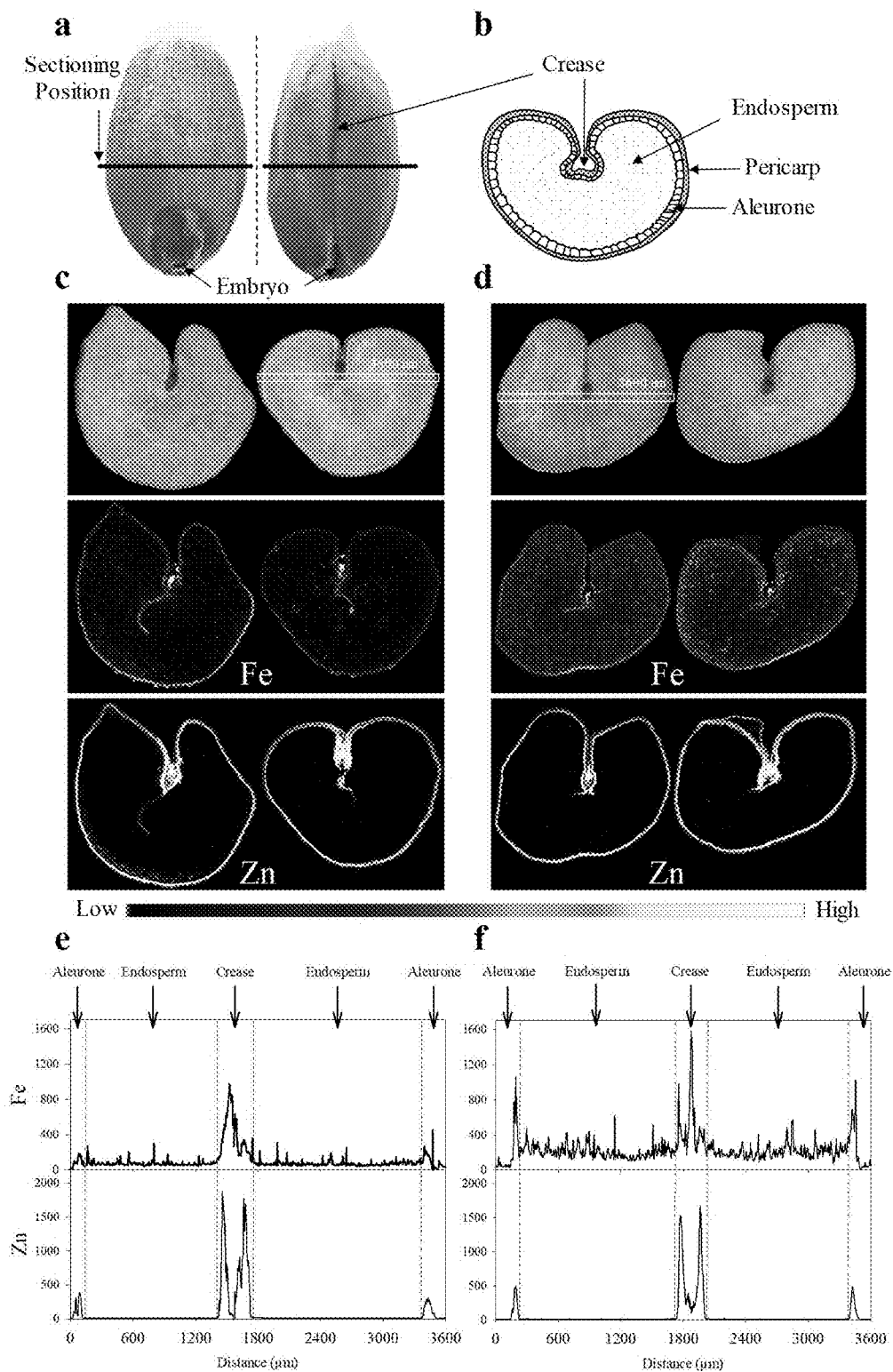
FIG. 3 shows distribution of iron and zinc in CE-OsNAS2 and NS wheat grain. (a) Position where transverse cross-sections of grain were made. (b) Diagram highlighting major tissues in a wheat grain transverse section. (c) Bright field images of two representative NS grain sections and corresponding XFM elemental maps of Fe and Zn. (d) Bright field images of two representative CE-1 grain sections and corresponding XFM elemental maps of Fe and Zn. Color bar represents high (white) and low (black) elemental concentration. White boxes in the bright field images represent areas in two grain sections (one each for NS and CE-1) used to generate line scans. (e) Line scans showing the distribution and signal intensity of Fe and Zn across NS grain. (f) Line scans showing the distribution and signal intensity of Fe and Zn across CE-1 grain. Units for the y-axis are elemental counts per pixel.

The resulting XRF maps showed that CE-1 grain had higher Fe signal intensities in all grain tissue types relative to NS with the largest difference detected in endosperm tissues (FIG. 3*c-d*). The Zn signal in both CE-1 and NS grain was localized to the aleurone and crease regions and was not detectable in the endosperm. Line scans across the midsection demonstrated that CE-1 grain had higher Fe signal intensities relative to NS in all regions of the grain, particularly in the endosperm, while CE-1 grain had slightly higher Zn signal intensities in the aleurone cells relative to NS (FIG. 3*e-f*). The lines scans also revealed different Fe and Zn distribution patterns within the crease region of NS and CE-1 grain, with Zn signals appearing as two distinct peaks on either side of the crease while Fe signals clustered into one central peak. While CE-1 and NS grain showed similar Zn signal intensities in the modified aleurone cells of the crease, the CE-1 grain had slightly higher Zn signal intensity in the nucellar projection relative to NS (FIG. 3*f*).

Figure 4:
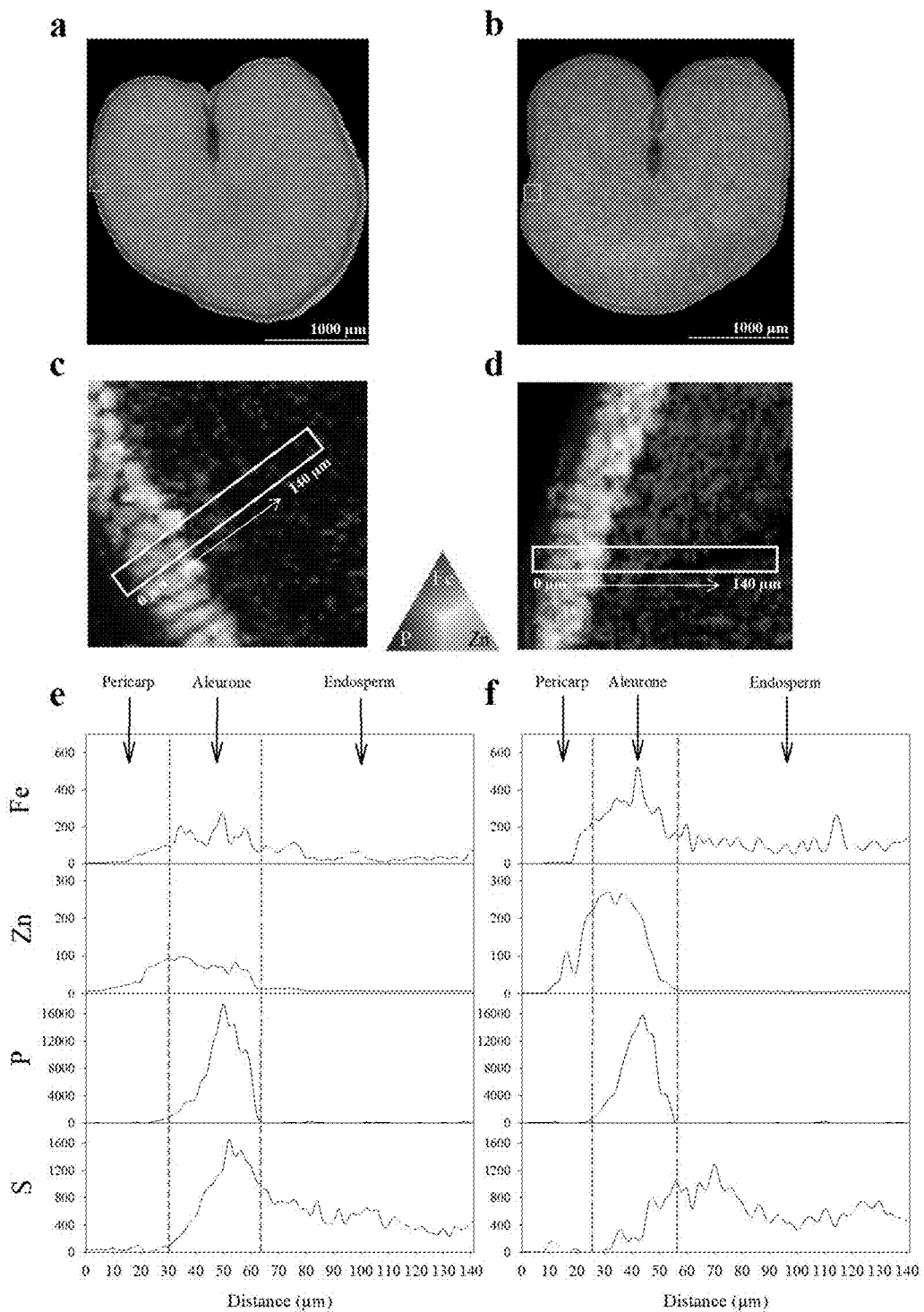
FIG. 4 shows distribution of iron, zinc, and phosphorus in CE-OsNAS2 and NS wheat grain. (a-b) Bright field images of NS and CE-1 grain sections, respectively. Yellow boxes represent areas used to generate tri-color elemental maps. (c) Tri-color XFM elemental map of Fe (red), Zn (green) and P (blue) in NS grain. White box represents the area used to generate line scans. (d) Tri-color XFM elemental map of Fe (red), Zn (green) and P (blue) in CE-1 grain. White box represents the area used to generate line scans. (e) Line scans showing the distribution and signal intensity of Fe, Zn, P and S in NS grain. (f) Line scans showing the distribution and signal intensity of Fe, Zn, P and S in CE-1 grain. Units for the y-axis are elemental counts per pixel.

Tri-color elemental maps of Fe, Zn and P near the grain edge of one representative CE-1 and NS grain demonstrated that the Fe signal in CE-1 grain was enhanced within pericarp, aleurone and endosperm regions relative to NS grain (FIG. 4*c-d*). The Zn signal in CE-1 grain was enhanced primarily within the pericarp and aleurone cells, relative to the NS, and co-localized with Fe in that region. The P signal in both NS and CE-1 grain did not differ in intensity nor distribution and was localized to the aleurone cells. The trends observed in CE-1 and NS tri-color maps were further confirmed by line scans (FIG. 4*e-f*). In both CE-1 and NS grain, P was localized exclusively to the aleurone cells with equal signal intensity, indicating that the significant enrichment of Fe in CE-1 endosperm was not associated with phytic acid (a P containing compound). The distribution and intensity of S (a proxy for protein) appeared slightly reduced in the CE-1 aleurone, relative to NS, but similar to NS in the endosperm (FIG. 4*e-f*).

Field trials were conducted in Western Australia in Merredin and Katanning. Grain were sown in 2 m² plots with three replicate plots per genotype and arranged in a randomized block design at each site. Rows were spaced at 30 cm and grain were sown at a rate of 60 kg ha$^{-1}$. At maturity, average plant height was determined from three representative measurements per plot and spike number, total biomass and TGW was determined from 0.15 m$^2$ subsamples per plot. Grain yield was calculated from the amount of grain harvested per 2 m$^2$ plot and extrapolated to kg/ha$^{-1}$. With the exception of CE-1.1 at Merredin, phenotype of the CE-1 sibling lines and NS did not differ with respect to plant height, spike number, biomass, thousand grain weight (TGW) and grain yield.

Example 3: Production and Characterization of Flour

Whole grain samples harvested at Merredin and Katanning were conditioned to 13% moisture content for 24 hr prior to milling. Each sample was milled using a Quadrumat Junior laboratory mill (Brabender, Duisburg, Germany) at constant temperature and run through a 280 μm sieve to isolate the white flour fraction. Average flour extraction for all lines from Merredin and Katanning was 71.5±0.2%.

Quantification of 6-aminoquinolyl-N-hydroxysuccinimidyl carbamate (AQC) derivatized NA in whole grain was performed via liquid chromatography-mass spectrometry (LC-MS). Quantification of 9-fluorenylmethoxycarboxyl chloride (FMOC-Cl) derivatized NA and DMA in whole grain and white flour was performed via RP LC-MS on an 1290 Infinity II and 6490 Triple Quadrupole LC/MS system (Agilent Technologies Inc.). Briefly, sequential methanol (100%) and deionized H$_2$O (18MΩ) extractions of pulverized wheat grain or white flour (25 mg) were combined and added (5 μL) to sodium borate buffer (pH=8, 1 M, 10 μL), EDTA buffer (pH=8, 50 mM, 10 μL) and fresh FMOC-Cl solutions (50 mM, 40 μL). After incubation (60° C., 700 rpm, 15 mins), the derivatization reaction was quenched via the addition of formic acid (FA; pH=4, 5%, 8.9 μL). A Zorbax Eclipse XDB-C18 Rapid Resolution HS 2.1×100 mm, 1.8 μm particle size column (Agilent Technologies Inc.) was used during chromatography with aqueous (0.1% v/v FA in dH$_2$O) and organic (0.1% v/v FA in acetonitrile) mobile phases. For quantification, a stock aqueous solution of NA and DMA (Toronto Research Chemicals) was prepared at 750 μM and a calibration set was generated in the range of 0.00504 to 75 μM.

Whole grain and white flour samples were digested for Caco-2 cell iron-bioavailability analysis. The Caco-2 cells were maintained in supplemented Dulbecco's modified Eagle medium (DMEM) for 11 days post-seeding and replaced with supplemented minimum essential media (MEM) solution 48 hr prior to the experiment. On the experiment day, gastric-digested samples (1.5 mL) were added to cylindrical Transwell inserts (Corning) fitted with a semipermeable (15000 Da MWCO) basal membrane (Spectra/Por 2.1, Spectrum Medical, Gardena, Calif.). The inserts were placed within wells containing Caco-2 cell monolayers and incubated for 2 hr (37° C.), after which the inserts were removed and additional MEM (1 mL) added to the cells before incubation for 22 hr (37° C.). After incubation, growth medium was removed by aspiration and the Caco-2 cells were washed twice with a solution (pH=7.0) containing NaCl (140 mmol/L), KCl (5 mmol/L) and PIPES (10 mmol/L) and harvested with the addition of deionized H$_2$O (1.5 mL) and brief sonication (Lab-Line Instruments, Melrose Park, Ill.). In an aliquot of the Caco-2 cell solution, ferritin content was determined using an immunoradiometric assay (FER-IRON II Ferritin Assay, Ramco Laboratories, Houston, Tex.) and total protein content was determined using a colorimetric assay (Bio-Rad DC Protein Assay, Bio-Rad, Hercules, Calif.). As Caco-2 cells synthesize ferritin in response to intracellular iron, we used the ratio of ferritin/total protein (expressed as ng ferritin/mg protein) as an index of cellular iron uptake.

Figure 5:
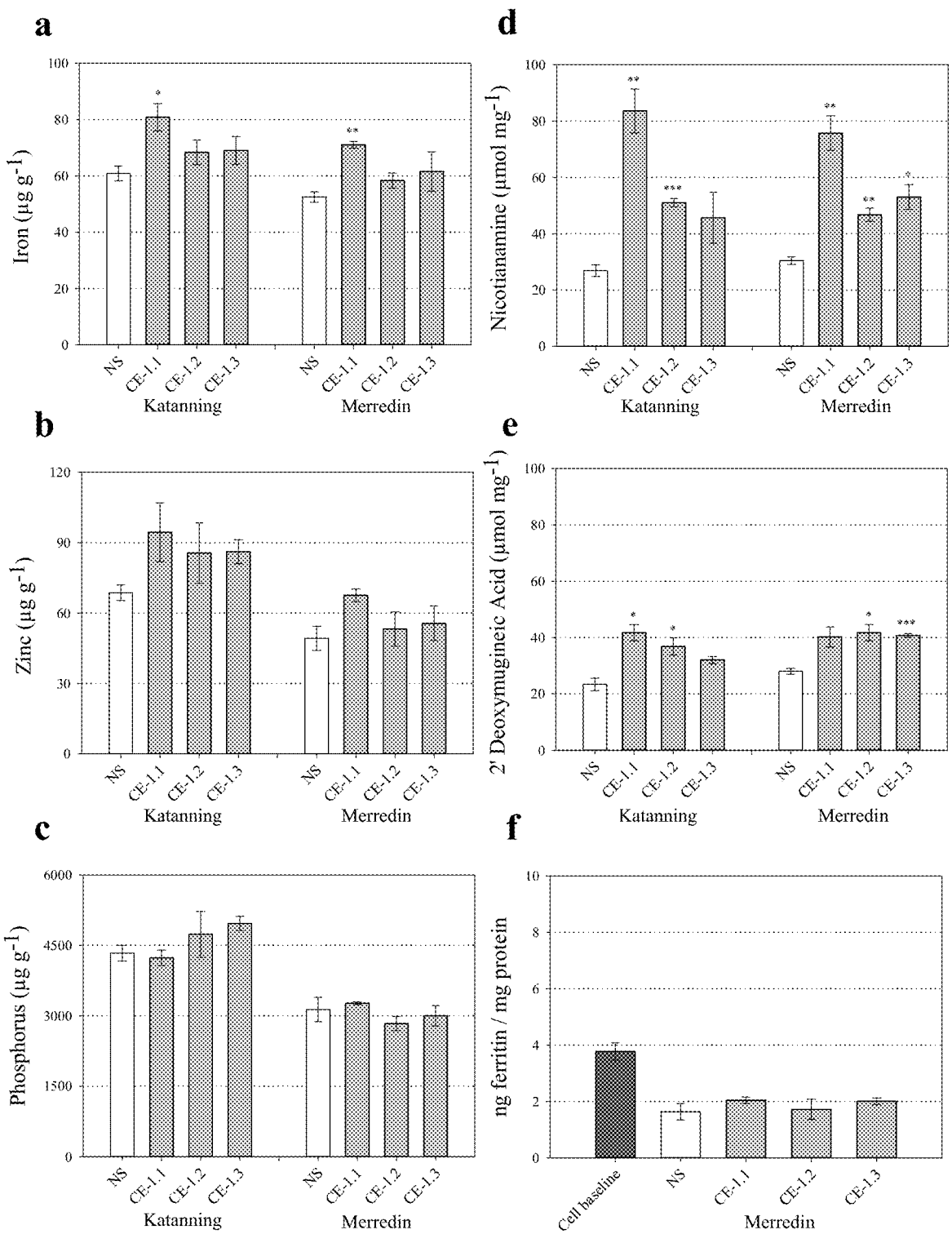
FIG. 5 shows whole grain nutrition of field grown CE-1 and NS wheat lines. Nutrient and metabolite concentrations in whole grain samples of NS (white) and three CE-1 sibling lines (CE-1.1, 1.2 and 1.3, grey) at the $T_6$ generation. (a-c) Whole grain Fe, Zn and P concentrations (μg g$^{-1}$) of NS and CE-1 plants grown at Katanning and Merredin field sites. (d-e) Whole grain NA and DMA concentrations (μmol mg$^{-1}$) of NS and CE-1 plants grown at Katanning and Merredin field sites. (f) Whole grain Fe bioavailability of NS and CE-1 plants grown at Merredin field site. Bars represent mean±SEM of 3 biological replicates. Asterisks denote the significance between NS and each CE-1 wheat line for P<0.05 (*), P≤0.01 (), P≤0.001 (*) as determined by student's t-test.

Whole grain zinc and phosphorus concentrations did not differ between the three CE-1 sibling lines and NS at both Merredin and Katanning. All lines (CE-1 and NS) had higher whole grain Zn and P concentrations at Katanning relative to Merredin, possibly due to lower TGW at Katanning (FIG. 5b-c). Analysis of NA and DMA showed that whole grain NA concentrations were significantly higher for CE-1.1 and CE-1.2 at Katanning (P=0.005 and P≤0.001, respectively), and for all three CE-1 sibling lines at Merredin (P=0.004, P=0.008 and P=0.016, respectively), relative to NS. Whole grain DMA concentrations were significantly higher for CE-1.1 and CE-1.2 at Katanning (P=0.014 and P=0.045, respectively), and CE-1.2 and CE-1.3 at Merredin (P=0.022 and P≤0.001, respectively), relative to NS (FIG. 5d-e).

Figure 6:
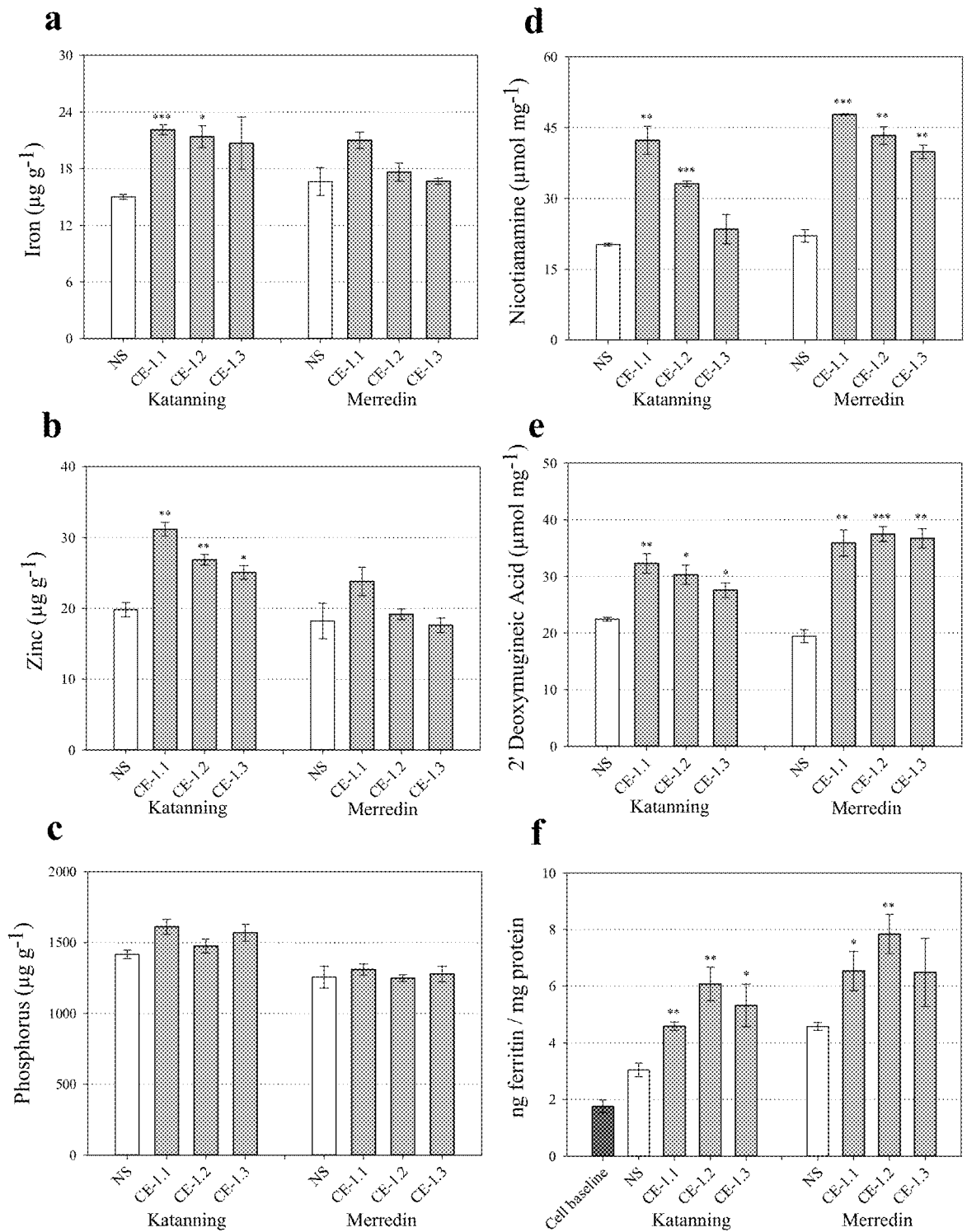
FIG. 6 shows white flour nutrition of field grown CE-1 and NS wheat lines. Nutrient and metabolite concentrations in white flour samples of NS (white) and three CE-1 sibling lines (CE-1.1, 1.2 and 1.3, grey) at the $T_6$ generation. (a-c) White flour Fe, Zn and P concentrations (μg g$^{-1}$) of NS and CE-1 plants grown at Katanning and Merredin field sites. (d-e) White flour NA and DMA concentrations (μmol mg$^{-1}$) of NS and CE-1 plants grown at Katanning and Merredin field sites. (f) White flour Fe bioavailability of NS and CE-1 plants grown at Merredin and Katanning field sites. Bars represent mean±SEM of 3 biological replicates. Asterisks denote the significance between NS and each CE-1 wheat line for P<0.05 (*), P≤0.01 (), P≤0.001 (*) as determined by student's t-test.

White flour iron concentrations were significantly higher for CE-1.1 and CE-1.2 at Katanning (P≤0.001 and P=0.012, respectively) relative to NS (FIG. 6a) but did not differ between any line at Merredin. White flour Zn concentrations were significantly higher for all three CE-1 sibling lines at Katanning (P=0.002, P=0.010 and P=0.036, respectively) relative to NS (FIG. 6b) but did not differ between any line at Merredin. White flour P concentration did not differ between any line at both Merredin and Katanning (FIG. 6a-c). White flour NA concentrations were significantly higher for CE-1.1 and CE-1.2 at Katanning (P=0.004 and P≤0.001, respectively) and for all three CE-1 sibling lines at Merredin (P≤0.001, P=0.002 and P=0.002, respectively), relative to NS (FIG. 6d). White flour DMA concentrations were significantly higher for all three CE-1 sibling lines at both Katanning (P=0.010, P=0.020 and P=0.035, respectively) and Merredin (P=0.006, P≤0.001 and P=0.002, respectively) relative to NS (FIG. 6e).

The levels of bioavailable iron in CE-1.1, CE-1.2, CE-1.3 and NS whole grain flour were negligible and did not differ significantly; a result likely due to phytic acid and other inhibitory compounds in the outer layers of wheat grain (FIG. 5f). By contrast, levels of bioavailable Fe were significantly increased in CE-1.1, CE-1.2, CE 1.3 white flour digests from Katanning (P=0.005, P=0.009 and P=0.045, respectively), and CE-1.1 and CE-1.2 white flour digests from Merredin (P=0.050 and P=0.010, respectively) relative to NS (FIG. 6f). White flour Fe bioavailability was significantly correlated with NA concentration (r=0.711, P=0.048) and DMA concentration (r=0.812, P=0.014).

Example 4: Animal Studies Design

The effects of NA-chelated iron, as opposed to free iron or EDTA-chelated iron were investigated. A chicken model was used as it is physiologically relevant for estimating dietary micronutrient absorption in other species and is generally used to evaluate iron and zinc bioavailability. Chicken eggs were injected intraamnioticly with water, an iron solution, Fe-EDTA solution, or a Fe-NA solution. Further, the results were directly compared against chickens fed with a control (white flour-based, prepared from NS wheat as described above) diet and chickens fed with a "biofortified" white flour, prepared from CE-OsNAS2 wheat grown in Merredin, as described above.

To generate extracts for administration, wheat flours (CE-OsNAS2, hereinafter "biofortified"; and NS, hereinafter "control") were mixed in dH$_2$O (50 g/L), filtered (600 μm)

and centrifuged, and the resulting supernatant was dialyzed (MWCO 12-14 kDa, Medicell International Ltd., London, UK) exhaustively against $dH_2O$ (48 hrs). The dialysate was lyophilized, and the resulting powder dissolved in 18MΩ $H_2O$ (0.05 g/mL) forming the white wheat flour extracts for intra-amniotic administration. Iron solutions were prepared by combining an Fe standard (1000 μg/mL, 2% HCl, High-Purity Standards, Charleston, S.C., USA) with either 18MΩ $H_2O$ (Fe), or 1.6 mM NA (Toronto Research Chemicals Inc., Toronto, Canada) dissolved in 18MΩ $H_2O$ (Fe-NA). The Fe-EDTA solution was achieved by combining ferric nitrate $(Fe(NO_3)_3 \cdot 9H_2O$, Sigma, St. Louis, Mo., USA) with hydroxyethyl ethylenediamine triacetic acid ($H_3$HEDTA, Sigma, St. Louis, Mo., USA) dissolved in sodium hydroxide (NaOH, Sigma, St. Louis, Mo., USA) to represent an anionic chelate of dissolved NaFeEDTA with final Fe concentration of 77 μM.

For creating feed compositions, a test feed was created using 80% biofortified white wheat flour and a control feed was created using 80% control white wheat flour. A dietary analysis of both feeds was conducted using known methods for iron, zinc, NA, DMA, phytate, fiber, protein, and carbon. The composition and dietary analysis of the feed compositions are shown in Table 2 below:

TABLE 2

Composition and analysis of the experimental diets. Component values represent mean ± SEM of at least four technical replicates. Asterisks denote significant differences for $p \leq 0.001$ (***) as determined by Student's t-test.

|  | Control | Biofortified |
|---|---|---|
|  | g/Kg (by formulation) | |
| Diet Ingredient | | |
| Control white wheat flour | 800 | — |
| Biofortified white wheat flour | — | 800 |
| skim milk, dry | 99.75 | 99.75 |
| DL-methionine | 2.5 | 2.5 |
| corn oil | 27 | 27 |
| choline chloride | 0.75 | 0.75 |
| vitamin/mineral premix (no Fe/Zn) | 70 | 70 |
| Selected Components | | |
| Dietary Fe (μg/g) | 25.9 ± 0.12 | 28.9 ± 0.13*** |
| Dietary Zn (μg/g) | 16.6 ± 0.06 | 19.2 ± 0.03*** |
| Dietary NA (μmol/g) | 18.1 ± 0.32 | 33.0 ± 0.21*** |
| Dietary DMA (μmol/g) | 19.5 ± 0.16 | 34.1 ± 0.74*** |
| Dietary Phytate (mg/g) | 0.5 ± 0.09 | 0.5 ± 0.08 |
| Total Fiber (μg/g) | 19.9 ± 0.18 | 23.8 ± 1.12 |
| Total Protein (%) | 13.47 ± 0.08 | 13.67 ± 0.08 |
| Total Carbon (%) | 41.90 ± 0.13 | 41.30 ± 0.13 |
| Phytate:Fe molar ratio | 1.63 | 1.46 |

Cornish-cross fertile broiler eggs (n=70) were obtained from a commercial hatchery (Moyer's chicks, Quakertown, Pa., USA) and incubated until hatching. All methods were performed in accordance with the relevant guidelines and regulations.

For intraamniotic administration, eggs (n=40) containing viable embryos were weighed and randomly assigned to seven groups (n≥5) based on weight distribution. At day 17 of incubation, extracts/Fe solutions (1 mL) were injected into the amniotic fluid via a 21-gauge needle for the seven treatment groups as follows: (1) non-injected (NI); (2) 18MΩ $H_2O$ ($H_2O$); (3) Fe solution (Fe); (4) Fe-EDTA solution (Fe-EDTA); (5) Fe-NA solution (Fe-NA); (6) Control white flour extract (C WF); (7) Biofortified white flour extract (B WF) and eggs were subsequently incubated for four days until hatch. Chicks were euthanized by $CO_2$ exposure after hatching and all tissues were collected.

The remaining hatchlings (n=30) were allocated based on body weight into two treatment groups: (1) 80% Control white flour diet and (2) 80% Biofortified white flour diet as described above. All chickens received a commercial diet (Nutrena® Chick Starter Grower 18% Crumble, Cargill Inc, Wayzata, Minn., USA) for one week prior to consumption of Control and Biofortified diets for six weeks. Control and Biofortified diet formulations met the Nutrient Requirements for Poultry (NRC Poultry reference) excluding Fe and Zn. Chickens (n=3) were housed in cages (1 m$^2$) and provided ad libitum access to food and $H_2O$. Feed intakes were measured daily, and body weight and blood samples were obtained weekly. Feed conversion ratio (FCR) represents weekly feed intake (g) proportional to the weekly increase in body weight (g). Chickens were euthanized by $CO_2$ exposure seven weeks post-hatch and tissues collected.

Analytics

Blood measurements. Wing-vein blood samples (100 μL) were collected using micro-hematocrit heparinized capillary tubes (Fisher, Pittsburgh, Pa., USA). Blood plasma Hb concentrations were determined spectrophotometrically using the Triton®/NaOH method according to manufacturer's instructions (Hemoglobin Assay Kit, Sigma, St. Louis, Mo., USA). The Hb maintenance efficiency (HME) was calculated as previously described[38]. Blood serum Linoleic Acid:Dihomo-γ-Linolenic Acid ratio (LA:DGLA) was determined as previously described.

Gene expression analysis. Total RNA extraction from duodenal and heart tissue (30 mg) using Qiagen RNeasy Mini Kit (RNeasy Mini Kit, Qiagen Inc., Valencia, Calif., USA), cDNA synthesis and real time-polymerase chain reaction (RT-PCR) analysis were performed. In brief, the cycle product (Cp) of each gene was quantified using a seven-point standard curve in duplicate. Gene expression was obtained relative to 18S (Cp), primer pair efficiency, and control treatments: NI for intraamniotic administration and Control for feeding trial. Alkaline phosphatase (AKP) and sucrase isomaltase (SI) acted as intestinal reference genes following intraamniotic administration.

Ferritin and glycogen analysis. Liver ferritin was determined using the following method: in brief, samples (1 g)

were homogenized in 4-(2-hydroxyethyl)-1-piperazineethanesulfonic acid (HEPES) buffer (50 mM) and heat treated (75° C., 10 min) before centrifugation. Native polyacrylamide gel electrophoresis (PAGE) gels were stained with Coomassie blue G-250 stain or potassium ferricyanide [$K_3Fe(CN)_6$] and quantified using the Quantity-One 1-D analysis program (Bio-Rad, Hercules, Calif.). Liver and pectoral glycogen was determined colorimetrically. After centrifugation and mixing with petroleum ether, homogenized tissue was mixed with color reagent (300 µL) and total glycogen determined on an ELISA plate reader (450 nm) according to a standard curve.

Intestinal functionality and short-chain fatty acid (SCFA) analysis. Duodenal samples were fixed in fresh 4% (v/v) buffered formaldehyde, dehydrated, and embedded in paraffin. Serial sections (5 µm) were deparaffinized in xylene and stained with hematoxylin and eosin before goblet cell number and villi surface area examination under light microscopy using EPIX XCAP software (Standard version, Olympus, Waltham, Mass., USA). Cecal samples were homogenized in HCl (2 ml, 3%, 1M), centrifuged and combined with ethyl acetate (100 µL) and acetic acid-d4 (1 µg/mL) before collecting the organic phase to determine short chain fatty acid (SCFA) composition. Samples were quantified via GC-MS using a TRACE™ 1310 gas chromatograph (Thermo Fisher Scientific, Waltham, Mass., USA) and a TraceGOLD™ TG-WaxMS A column (Thermo Fisher Scientific, Waltham, Mass., USA).

Microbial population analysis. *Lactobacillus, Bifidobacterium, Escherichia*, and *Clostridium* density in intraamniotic administration treatment groups was determined as follows: in brief, cecal contents were homogenized with phosphate-buffered saline (PBS, 9 ml), centrifuged and the pellet resuspended in ethylenediaminetetraacetic acid (EDTA, 50 mM) and treated (37° C., 45 min) with lysozyme (10 mg/mL, Sigma Aldrich CO., St. Louis, Mo., USA). Bacterial genomic DNA was isolated according to manufacturer's instructions (Wizard® Genomic DNA Purification Kit, Promega Corp., Madison, Wis., USA) and bacterial genera are presented in relative proportions.

16S rRNA gene sequencing and analysis. Microbial genomic DNA extraction from Control and Biofortified cecal samples, gene sequencing and analysis were conducted. In brief, 16S rRNA gene sequences were amplified from the V4 hypervariable region of microbial genomic DNA (Powersoil DNA isolation kit, MoBio Laboratories Ltd., Carlsbad, Calif., USA), purified (AMPure, Beckman Coulter, Atlanta, Ga., USA), and quantified according to manufacturer's instructions (Quant-iT™ PicoGreen™ dsDNA Assay Kit, Invitrogen, Carlsbad, Calif., USA). Samples were sequenced using an Illumina MiSeq Sequencer (Illumina, Inc., Madison, Wis., USA). Amplicon reads were analyzed using Divisive Amplicon Denoising Algorithm (DADA2) and quantitative insights into microbial ecology (QIIME) software before taxonomic classification using Greengenes database. Faith's phylogenetic diversity (PD) was used to assess α-diversity and principal component (PC) analysis of weighted UniFrac distances was used to assess β-diversity. Relative abundance was determined using linear discriminant analysis effect size (LEfSe) and metabolic capacity was determined using phylogenetic investigation of communities by reconstruction of unobserved states (PICRUSt) software compared to known pathways in the Kyoto Encyclopedia of Genes and Genomes (KEGG) database.

Example 5: Relation of NA-Chelated Iron to Gut Health

Figure 7:
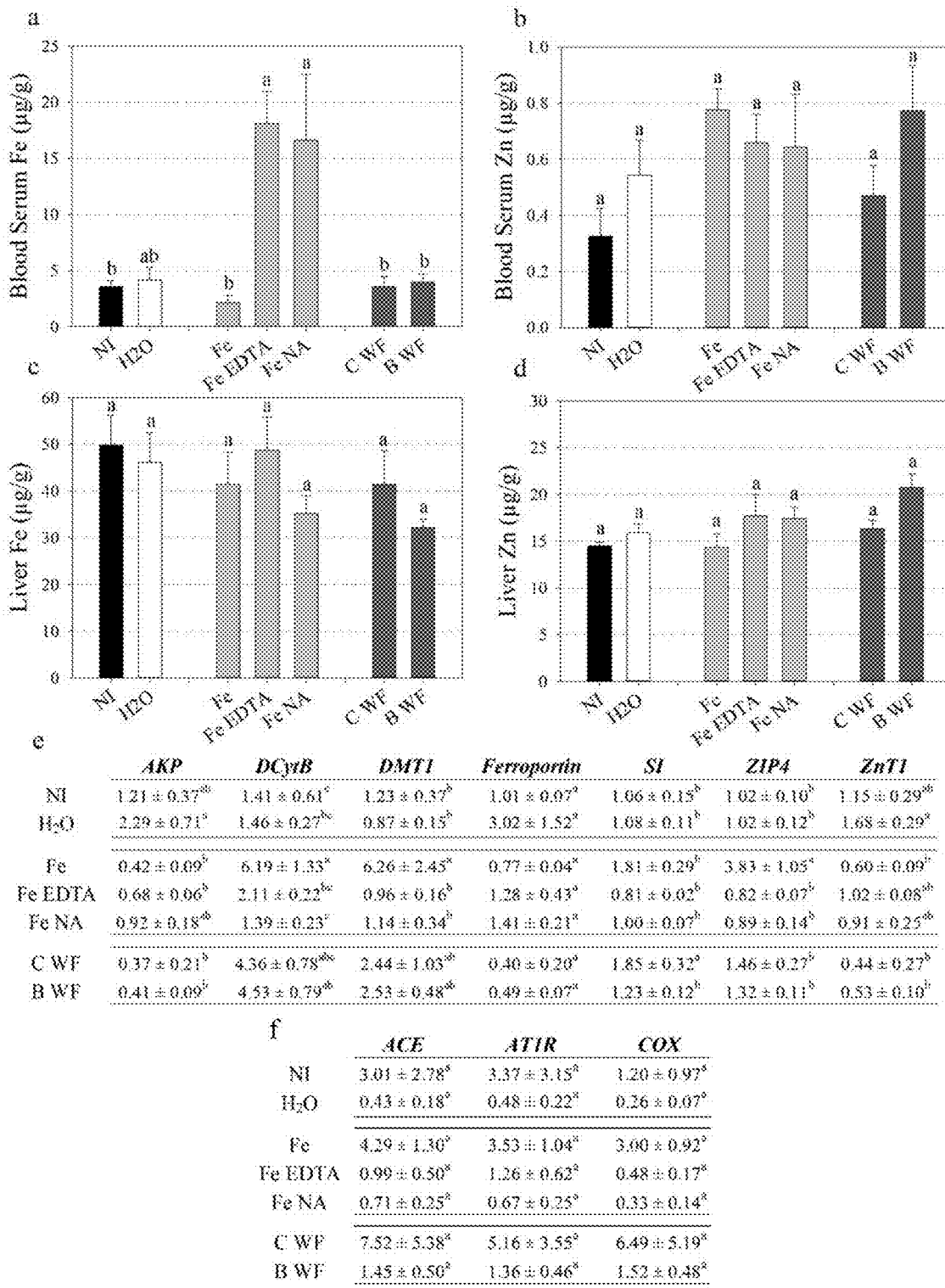
FIG. 7 shows biomarkers of Fe and Zn status following intraamniotic administration. Fe and Zn concentration (μ/g) in chicken (a-b) blood serum, respectively; and (c-d) liver, respectively. Bars represent mean±SEM of at least three biological replicates. (e-f) Transcript quantification of genes in chicken duodenal and heart tissue, respectively. Values (expression ratio relative to 18S) represent mean±SEM of at least three biological replicates, each with two technical replicates of quantitative RT-PCR. Different letters indicate significantly different values between treatment groups as analyzed by one-way ANOVA with Tukey post-hoc test (p<0.05). NI: non-injected, C WF: control white flour extract, B WF: biofortified white flour extract.

Blood serum Fe concentration was significantly elevated in chickens that received intraamniotic administration of EDTA-chelated Fe and NA-chelated Fe relative to unchelated Fe (Fe) and non-injected treatment groups (FIG. 7A). Blood serum Zn and liver Fe concentrations were not significantly different between treatment groups (FIG. 7B-C).

Duodenal cytochrome B (DcytB), divalent metal transporter 1 (DMT1), and Zn transporter (ZIP4) expression were significantly upregulated in intestinal tissue of chickens that received Fe relative to all treatment groups, except for DcytB and DMT1 expression in control white flour extract (C-WF) and biofortified white flour extract (B-WF) treatment groups (FIG. 7E). Both alkaline phosphatase (AKP) and Zn transporter 1 (ZnT1) expression were significantly upregulated in chickens that received intraamniotic administration of $H_2O$ ($H_2O$) relative to Fe, C-WF and B-WF treatment groups (FIG. 7E). No differences in heart gene expression were observed between treatment groups (FIG. 7F).

Figure 8:
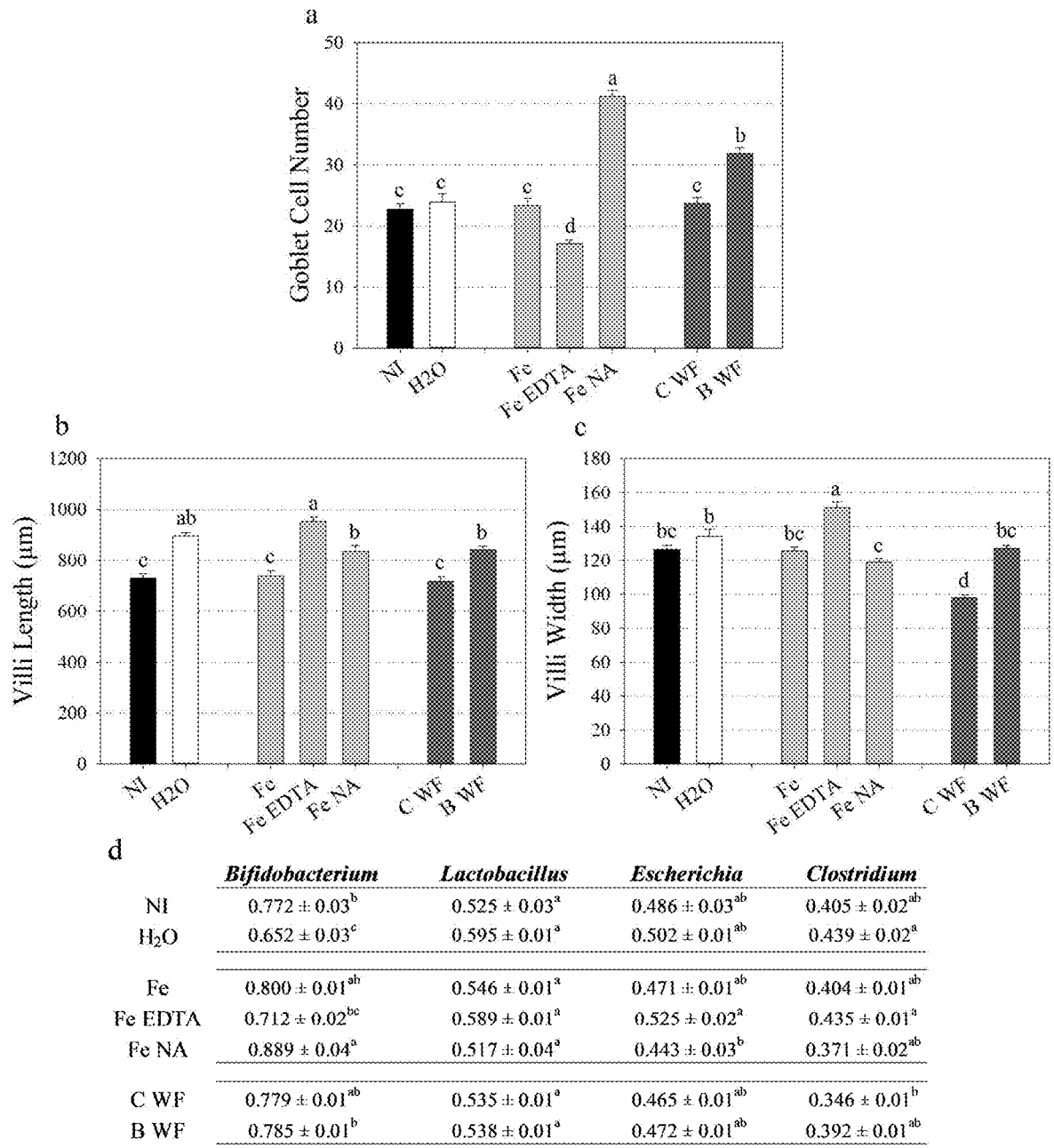
FIG. 8 shows intestinal functionality and cecal microbial composition following intraamniotic administration. (a) Chicken intestinal goblet cell number. (b-c) Chicken intestinal villi length and width (μm), respectively. Bars represent mean±SEM of five biological replicates. (d) Bacterial proportions relative to a universal bacterial population present in ceca. Values represent mean±SEM of five biological replicates. Different letters indicate significantly different values between treatment groups as analyzed by one-way ANOVA with Tukey post-hoc test (p<0.05). NI: non-injected, C-WF: control white flour extract, B-WF: biofortified white flour extract.

Goblet cell number increased significantly in Fe-NA intestinal villi relative to all treatment groups and in B-WF relative to all groups except for Fe-NA (FIG. 8A). Goblet cell number decreased significantly in Fe-EDTA intestinal villi relative to all treatment groups. Intestinal villi length increased significantly in Fe-EDTA relative to all treatment groups except for $H_2O$ and in $H_2O$, Fe-NA and B-WF treatment groups relative to NI, Fe and B-WF treatment groups (FIG. 8B). Intestinal villi width increased significantly in Fe-EDTA relative to all treatment groups, and in $H_2O$ relative to Fe-NA (FIG. 8C). Intestinal villi width decreased significantly in C-WF relative to all treatment groups.

The abundance of *Bifidobacterium* significantly increased in Fe-NA cecum relative to all treatment groups apart from Fe and C-WF, and significantly decreased in $H_2O$ relative to all treatment groups apart from Fe-EDTA (FIG. 8D). The abundance of both *Escherichia* significantly increased in Fe-EDTA cecum relative to Fe-NA and *Clostridium* significantly increased in $H_2O$ and Fe-EDTA relative to C-WF (FIG. 8D).

Example 6: Feeding Trial of Biofortified Wheat Flour

As seen in Table 2 above, the concentrations of Fe, Zn, NA and DMA were significantly higher in white flour derived from field-grown bread wheat expressing the rice nicotianamine synthase (OsNAS2) gene compared to control white flour and significantly increased 1.1- to 1.2-fold (Fe and Zn) and 1.7- to 1.8-fold (NA and DMA) in diet containing 80% biofortified white flour relative to diet containing 80% control white flour. Caco-2 cell ferritin significantly increased after exposure to biofortified white flour relative to control white flour (Data not shown). At week 2, hemoglobin (Hb), total body Hb and hemoglobin maintenance efficiency (HME) decreased significantly in Biofortified relative to Control chickens (FIG. 9). From week 4 onwards, a trend of lower cumulative feed intake (g) and cumulative feed conversion ratio (FCR) was present in Biofortified relative to Control chickens. No differences in body weight between Biofortified and Control chickens were observed throughout the study (FIG. 9).

Figure 10:
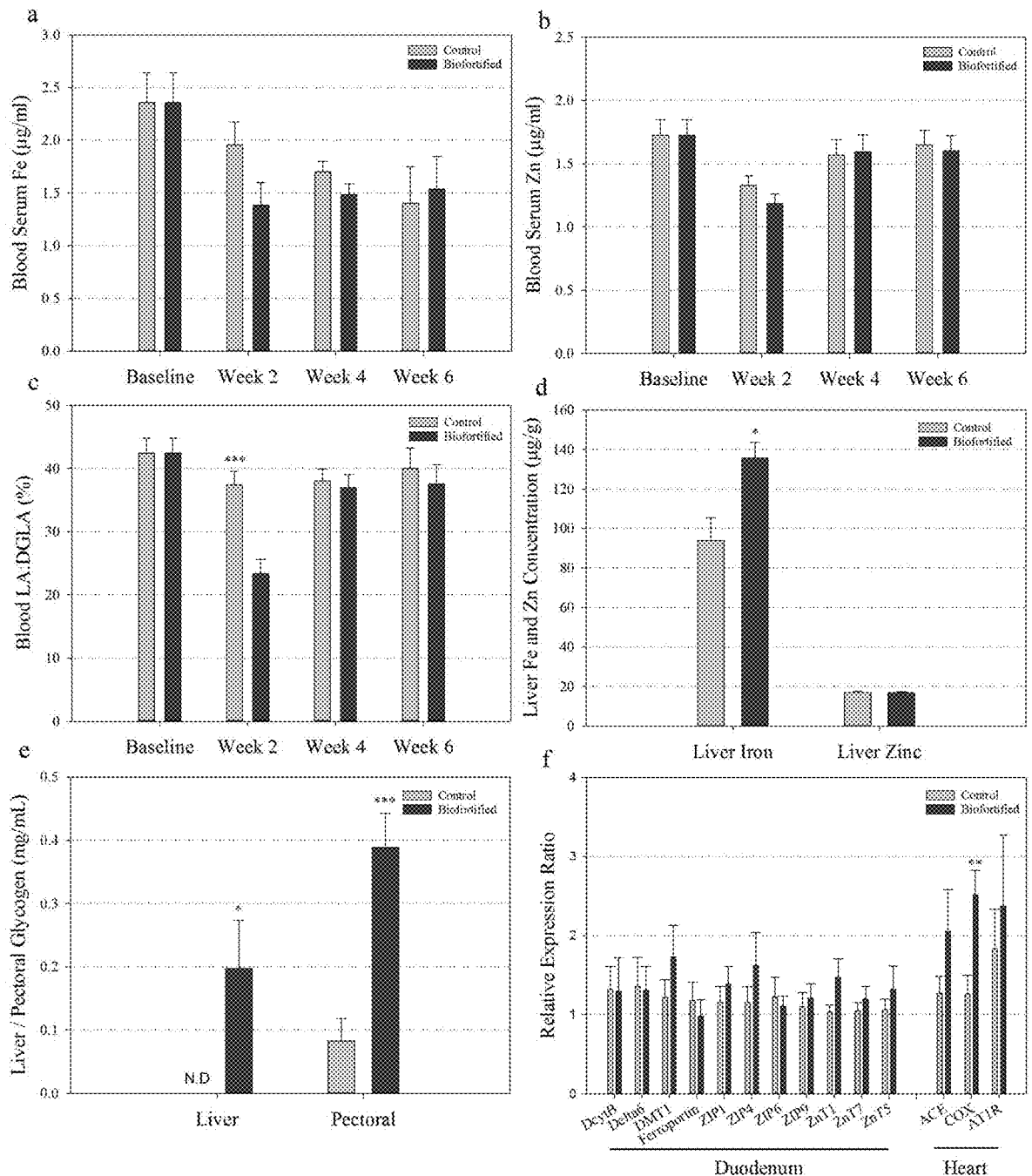
FIG. 10 shows the status of biomarkers of Fe and Zn and glycogen storage following consumption of experimental diets. (a-b) Fe and Zn concentration (μg/g) in chicken blood serum, respectively. (c) Ratio of LA:DGLA in chicken blood cells. Measurements were taken at the beginning (Baseline) and in the $2^{nd}$, $4^{th}$ and $6^{th}$ week of the study. (d) Fe and Zn concentration (μg/g) in chicken liver. (e) Glycogen (mg/mL) concentration in chicken liver and pectoral tissue. Bars represent mean±SEM of nine biological replicates. (f) Relative transcript quantification in chicken duodenal and heart tissue. Bars represent mean±SEM of at least eight biological replicates, each with two technical replicates of quantitative RT-PCR. Asterisks denote significant differences for p<0.05 (*), p<0.001 (***) as determined by Student's t-test.

No differences in blood serum Fe and Zn concentrations were observed between Biofortified and Control chickens throughout the study (FIG. 10A-B). At week 2, blood linoleic acid:dihomo-γ-linolenic acid ratio (LA:DGLA) was significantly decreased in Biofortified relative to Control chickens (FIG. 10C). At the conclusion of the study, liver Fe concentration and glycogen storage in both liver and pectoral tissue was significantly elevated in Biofortified relative to Control chickens (FIG. 10D-E). Expression of COX was significantly upregulated in Biofortified heart tissue relative to Control (FIG. 10F).

Figure 11A:
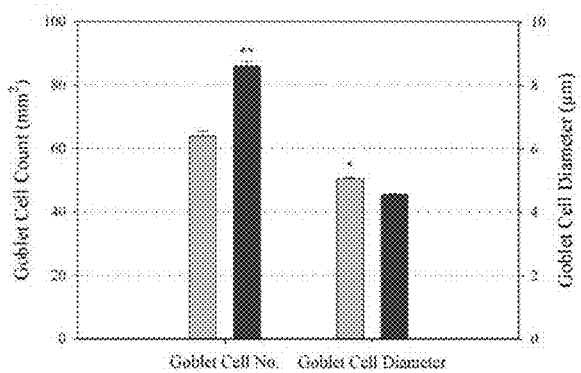
FIGS. 11A-11E show intestinal functionality, short-chain fatty acid production and cecal microbial composition following consumption of experimental diets.
Figure 11B:
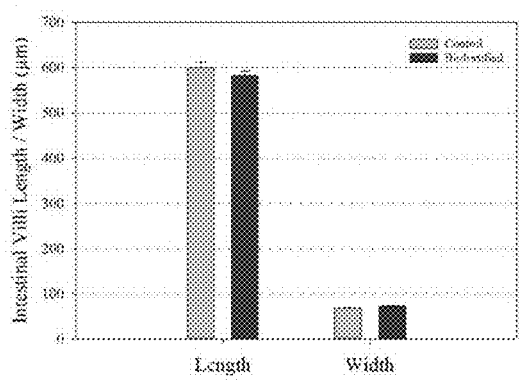
Figure 11C:
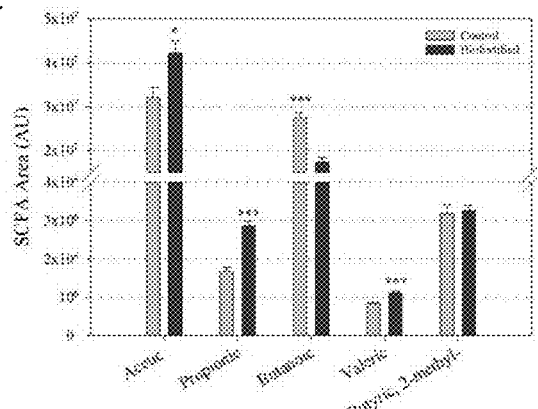
Figure 11D:
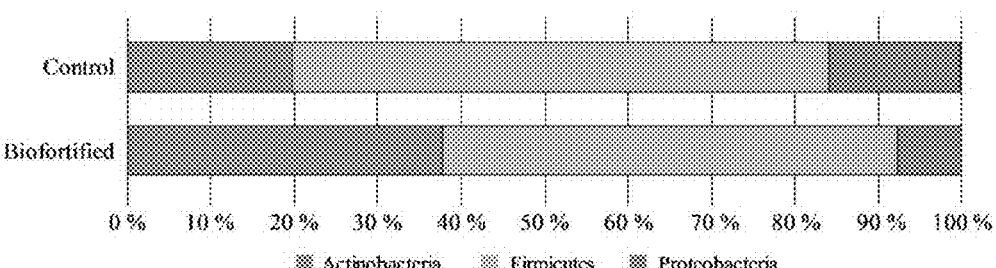
Figure 11E:
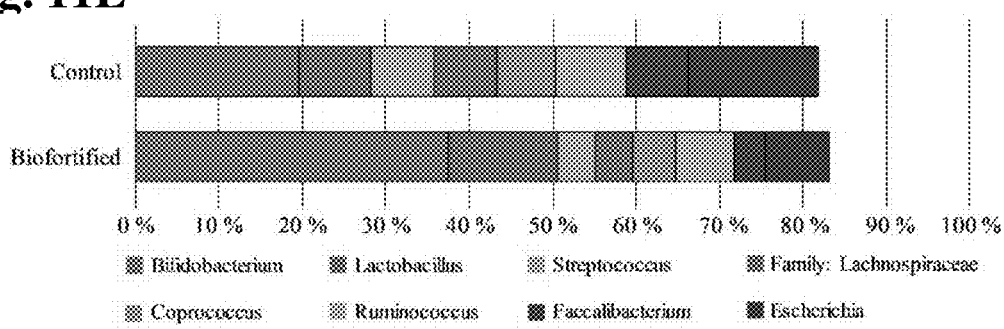

It was found that the biofortified white wheat flour increases goblet cell number and positively altered gut health and the microbiome. The number of intestinal goblet cells significantly increased, and the diameter of intestinal goblet cells significantly decreased in Biofortified relative to Control chickens (FIG. 11A). No difference in intestinal villi length and width was detected (FIG. 11B). Short-chain fatty acid (SCFA) production significantly increased for acetic acid, propionic acid and valeric acid and decreased for butanoic acid in Biofortified relative to Control chickens (FIG. 11C). For major bacteria phyla the proportion of Actinobacteria increased 1.9-fold while the proportion of Firmicutes and Proteobacteria decreased 1.2- and 2.0-fold, respectively in Biofortified ceca relative to Control (FIG. 11D). For major bacterial genera the proportion of *Bifidobacterium* and *Lactobacillus* increased 1.9- and 1.5-fold, respectively while the proportion of *Streptococcus* (1.7-fold), *Coprococcus* (1.4-fold), *Ruminococcus* (1.2-fold) *Faecalibacterium* (2-fold), and *Escherichia* (2-fold) decreased in Biofortified relative to Control (FIG. 11D). The proportion of family Lachnospiraceae decreased 1.7-fold and was significantly (p=0.045) lower in Biofortified relative to Control (FIG. 11D). Only one genus, *Enterococcus*, was significantly (p=0.010) more abundant in Biofortified (3.5%) relative to Control (>1.0%). The abundance of all families and genera detected decreased 1.5-fold in Biofortified cecum relative to Control.

Figure 12A:
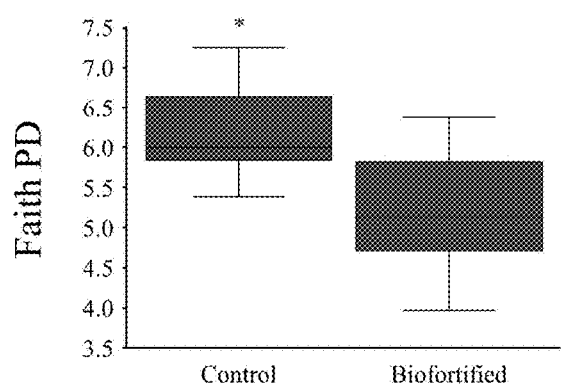
FIGS. 12A-12C show microbial diversity and metabolic capacity following consumption of experimental diets.
Figure 12B:
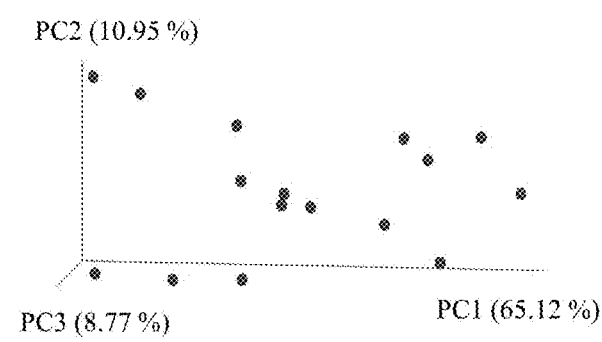
Figure 12C:
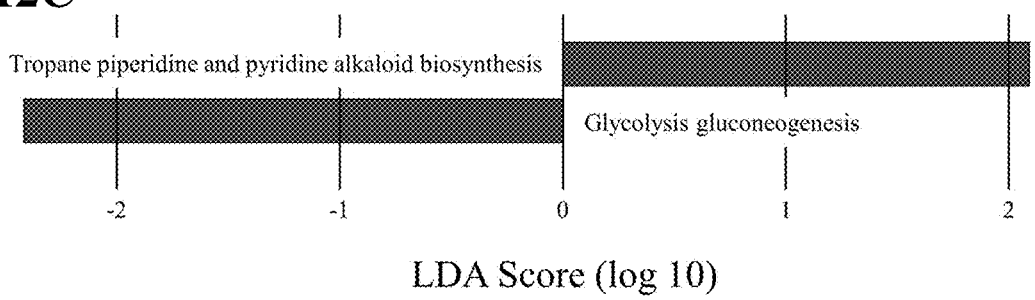

It was also found that biofortified white wheat flour significantly altered diversity and metagenomic potential of the intestinal microbiota. Microbial population diversity (α-diversity) represented as Faith's phylogenetic diversity significantly decreased in Biofortified cecum relative to Control (FIG. 12A). Significant (q=0.042) separate clustering (β-diversity) of weighted Biofortified and Control microbial populations was observed (FIG. 12B) with family Enterococcaceae (including an unspecified genus) significantly more abundant and genus *Dorea* significantly less abundant in Biofortified relative to Control. Microbial glycolysis/gluconeogenesis significantly increased and microbial tropane piperidine and pyridine alkaloid biosynthesis significantly decreased in Biofortified microbial populations relative to Control (FIG. 12C).

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. A method of decreasing a feed conversion ratio (FCR) in avians,
    the method comprising delivering to an avian a feed composition comprising an effective amount of biofortified grain flour for at least four weeks,
    wherein the biofortified grain flour has a concentration of nicotianamine of at least 25 μmol/g.

2. The method of claim 1, wherein the delivering to the avian the feed composition comprising an effective amount of biofortified grain flour is for at least six weeks.

3. The method of claim 1, wherein the biofortified grain flour has a concentration of nicotianamine of at least 30 μmol/g.

4. The method of claim 1, wherein after four weeks of feeding, the FCR has been decreased by at least 12.5% relative to an avian delivered a feed composition which does not comprise biofortified grain flour.

5. The method of claim 1, wherein the grain is wheat.

* * * * *